(12) United States Patent
Dacquay et al.

(10) Patent No.: US 8,182,435 B2
(45) Date of Patent: May 22, 2012

(54) INTRAOCULAR PRESSURE SENSOR

(75) Inventors: Bruno Dacquay, Irvin, CA (US);
Matthew J. A. Rickard, Tustin, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 271 days.

(21) Appl. No.: 12/434,709

(22) Filed: May 4, 2009

(65) Prior Publication Data
US 2010/0280349 A1    Nov. 4, 2010

(51) Int. Cl.
| A61B 3/16 | (2006.01) |
| A61B 5/103 | (2006.01) |
| A61B 5/117 | (2006.01) |
| G01L 7/00 | (2006.01) |
| G01L 19/04 | (2006.01) |
| G01L 7/08 | (2006.01) |
| G01L 9/02 | (2006.01) |
| G01L 9/00 | (2006.01) |

(52) U.S. Cl. ............ 600/591; 600/398; 73/700; 73/708; 73/715; 73/716; 73/717; 73/719; 73/720; 73/721; 73/723; 73/725; 73/726; 73/727

(58) Field of Classification Search .......... 600/398, 600/591; 73/700, 708, 715–717, 719–721, 73/723, 725–727
See application file for complete search history.

(56) References Cited

U.S. PATENT DOCUMENTS

| 4,089,329 A | 5/1978 | Couvillon et al. |
| 4,457,757 A | 7/1984 | Molteno |
| 4,750,901 A | 6/1988 | Molteno |
| 4,922,913 A | 5/1990 | Waters et al. |
| 5,005,577 A | 4/1991 | Frenkel |
| 5,178,604 A | 1/1993 | Baerveldt |
| 5,179,953 A | 1/1993 | Kursar |
| 5,397,300 A | 3/1995 | Baerveldt |
| 5,476,445 A | 12/1995 | Baerveldt |
| 5,558,629 A | 9/1996 | Baerveldt |
| 6,447,449 B1 * | 9/2002 | Fleischman et al. .......... 600/405 |
| 6,589,198 B1 | 7/2003 | Soltanpour et al. |

(Continued)

FOREIGN PATENT DOCUMENTS
DE    4438201    5/1996
(Continued)

OTHER PUBLICATIONS

Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May, 2002 DOI 10.1007/s00417-002-0474-y; pp. 335-336; Subject Collection Medicine.

(Continued)

Primary Examiner — Max Hindenburg
Assistant Examiner — Sean Dougherty
(74) Attorney, Agent, or Firm — Kenneth D. Bassinger

(57) ABSTRACT

An implantable intraocular pressure sensor system has a sealed geometric shape with an internal pressure at a first value. A strain gauge wire is embedded in a surface of the sealed geometric shape. When the surface is deflected by intraocular pressure, a measured resistance of the strain gauge wire indicates the intraocular pressure. The system also has a processor coupled to a power source and memory. The processor is configured to read the measured resistance and write values corresponding to intraocular pressure to the memory.

16 Claims, 3 Drawing Sheets

U.S. PATENT DOCUMENTS

| | | | |
|---|---|---|---|
| 6,712,764 | B2 | 3/2004 | Jeffries et al. |
| 6,749,568 | B2 | 6/2004 | Fleischman et al. |
| 6,939,299 | B1 | 9/2005 | Petersen et al. |
| 7,137,952 | B2 | 11/2006 | Leonardi et al. |
| 7,169,106 | B2 | 1/2007 | Fleischman et al. |
| 7,252,006 | B2 | 8/2007 | Tai et al. |
| 7,354,416 | B2 | 4/2008 | Quiroz-Mercado et al. |
| 7,409,863 | B2 | 8/2008 | Bateman et al. |
| 7,612,328 | B2 | 11/2009 | Kaiser |
| 2001/0000527 | A1 | 4/2001 | Yaron et al. |
| 2002/0143284 | A1 | 10/2002 | Tu et al. |
| 2002/0193674 | A1* | 12/2002 | Fleischman et al. .......... 600/399 |
| 2003/0078487 | A1 | 4/2003 | Jeffries |
| 2003/0225318 | A1 | 12/2003 | Montegrande et al. |
| 2004/0059248 | A1 | 3/2004 | Messner et al. |
| 2004/0073137 | A1 | 4/2004 | Lloyd et al. |
| 2004/0116794 | A1 | 6/2004 | Fink et al. |
| 2004/0254438 | A1 | 12/2004 | Chuck et al. |
| 2005/0159660 | A1 | 7/2005 | Montegrande et al. |
| 2005/0271704 | A1 | 12/2005 | Tu et al. |
| 2005/0273033 | A1 | 12/2005 | Grahn et al. |
| 2007/0109117 | A1* | 5/2007 | Heitzmann et al. ...... 340/539.12 |
| 2007/0123767 | A1* | 5/2007 | Montegrande et al. ....... 600/398 |
| 2007/0129623 | A1* | 6/2007 | Fleischman et al. .......... 600/398 |
| 2008/0015421 | A1* | 1/2008 | Penner .......................... 600/300 |
| 2008/0129486 | A1* | 6/2008 | Jeckelmann et al. .... 340/539.12 |
| 2008/0228127 | A1 | 9/2008 | Burns et al. |
| 2009/0069648 | A1 | 3/2009 | Irazqui et al. |
| 2009/0076367 | A1 | 3/2009 | Sit et al. |
| 2009/0227933 | A1 | 9/2009 | Karageozian |
| 2009/0275924 | A1* | 11/2009 | Lattanzio et al. .......... 604/891.1 |
| 2010/0010416 | A1 | 1/2010 | Juan, Jr. et al. |
| 2010/0042209 | A1 | 2/2010 | Guarnieri |
| 2010/0121348 | A1 | 5/2010 | Van Der Burg et al. |
| 2010/0234717 | A1 | 9/2010 | Wismer |
| 2010/0253167 | A1 | 10/2010 | Charnley et al. |

FOREIGN PATENT DOCUMENTS

| | | |
|---|---|---|
| WO | WO 98/03665 | 4/1993 |
| WO | WO 03/102632 | 12/2003 |
| WO | WO 2009/081031 | 7/2009 |

OTHER PUBLICATIONS

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

Leonard!, Matteo, et al., "A Soft Contact Lens With a Mems Strain Gage Embedded For Intraocular Pressure Monitoring," In Proc. 12th Int'l Conference on Solid State Sensors, Actuators and Microsystems, Jun. 8-12, 2003, pp. 1043-1046, vol. 2, Boston, MA.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.

Van Schuylenbergh, K., et al, "An Implantable Telemetric Tonometer For Direct Intraocular Pressure Measurements," 1st European Conference on Biomedical Engineering, Feb. 1991, pp. 194-195, vol. 17, No. 20, Nice, France.

Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.

McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Schnakenberg, U., et al, "Initial Investigations on Systems for Measuring Intraocular Pressure," Sensors and Actuators, 2000, p. 287-291, vol. 85, Elsevier Science B.V., Germany.

Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470- 474, Lyon, France.

Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.

Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.

* cited by examiner

INTRAOCULAR PRESSURE SENSOR

BACKGROUND OF THE INVENTION

The present invention relates to a device for monitoring intraocular pressure and more particularly to an implantable pressure sensor.

Glaucoma, a group of eye diseases affecting the retina and optic nerve, is one of the leading causes of blindness worldwide. Glaucoma results when the intraocular pressure (IOP) increases to pressures above normal for prolonged periods of time. IOP can increase due to an imbalance of the production of aqueous humor and the drainage of the aqueous humor. Left untreated, an elevated IOP causes irreversible damage the optic nerve and retinal fibers resulting in a progressive, permanent loss of vision.

The eye's ciliary body epithelium constantly produces aqueous humor, the clear fluid that fills the anterior chamber of the eye (the space between the cornea and iris). The aqueous humor flows out of the anterior chamber through the uveoscleral pathways, a complex drainage system. The delicate balance between the production and drainage of aqueous humor determines the eye's IOP.

Open angle (also called chronic open angle or primary open angle) is the most common type of glaucoma. With this type, even though the anterior structures of the eye appear normal, aqueous fluid builds within the anterior chamber, causing the IOP to become elevated. Left untreated, this may result in permanent damage of the optic nerve and retina. Eye drops are generally prescribed to lower the eye pressure. In some cases, surgery is performed if the IOP cannot be adequately controlled with medical therapy.

Only about 10% of the population suffers from acute angle closure glaucoma. Acute angle closure occurs because of an abnormality of the structures in the front of the eye. In most of these cases, the space between the iris and cornea is more narrow than normal, leaving a smaller channel for the aqueous to pass through. If the flow of aqueous becomes completely blocked, the IOP rises sharply, causing a sudden angle closure attack.

Secondary glaucoma occurs as a result of another disease or problem within the eye such as: inflammation, trauma, previous surgery, diabetes, tumor, and certain medications. For this type, both the glaucoma and the underlying problem must be treated.

FIG. 1 is a diagram of the front portion of an eye that helps to explain the processes of glaucoma. In FIG. 1, representations of the lens 110, cornea 120, iris 130, ciliary bodies 140, trabecular meshwork 150, and Schlemm's canal 160 are pictured. Anatomically, the anterior chamber of the eye includes the structures that cause glaucoma. Aqueous fluid is produced by the ciliary bodies 140 that lie beneath the iris 130 and adjacent to the lens 110 in the anterior chamber. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The first structure, and the one most commonly implicated in glaucoma, is the trabecular meshwork 150. The trabecular meshwork 150 extends circumferentially around the anterior chamber in the angle. The trabecular meshwork 150 seems to act as a filter, limiting the outflow of aqueous humor and providing a back pressure producing the IOP. Schlemm's canal 160 is located beyond the trabecular meshwork 150. Schlemm's canal 160 has collector channels that allow aqueous humor to flow out of the anterior chamber. The two arrows in the anterior chamber of FIG. 1 show the flow of aqueous humor from the ciliary bodies 140, over the lens 110, over the iris 130, through the trabecular meshwork 150, and into Schlemm's canal 160 and its collector channels.

In glaucoma patients, IOP can vary widely during a 24 hour period. Generally, IOP is highest in the early morning hours before medication is administered upon waking. Higher pressures damage the optic nerve and can lead to blindness. Accordingly, it would be desirable to measure IOP over time in order to assess the efficacy of various treatments. The present invention provides an IOP measuring device.

SUMMARY OF THE INVENTION

In one embodiment consistent with the principles of the present invention, the present invention is an implantable intraocular pressure sensor system that has a sealed geometric shape with an internal pressure at a first value. A strain gauge wire is embedded in a surface of the sealed geometric shape. When the surface is deflected a measured resistance of the strain gauge wire indicates an intraocular pressure.

In another embodiment consistent with the principles of the present invention, the present invention is an implantable intraocular pressure sensor system that has a sealed geometric shape with an internal pressure at a first value. A strain gauge wire is embedded in a surface of the sealed geometric shape. When the surface is deflected by intraocular pressure, a measured resistance of the strain gauge wire indicates the intraocular pressure. The system also has a processor coupled to a power source and memory. The processor is configured to read the measured resistance and write values corresponding to intraocular pressure to the memory.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
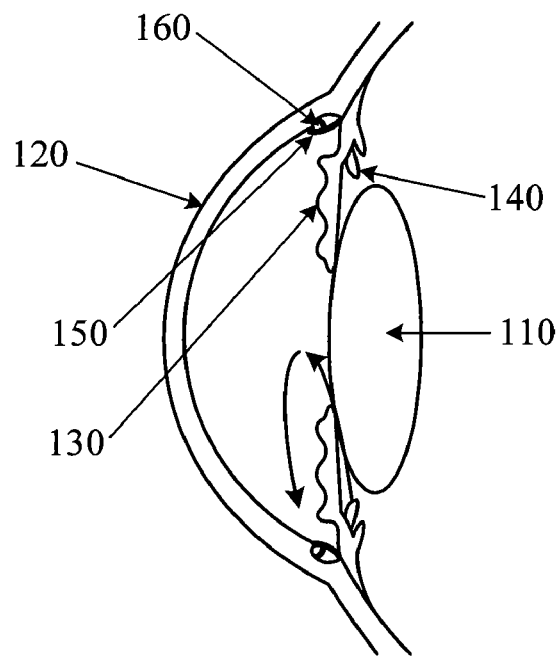
FIG. 1 is a diagram of the front portion of an eye.
Figure 2:
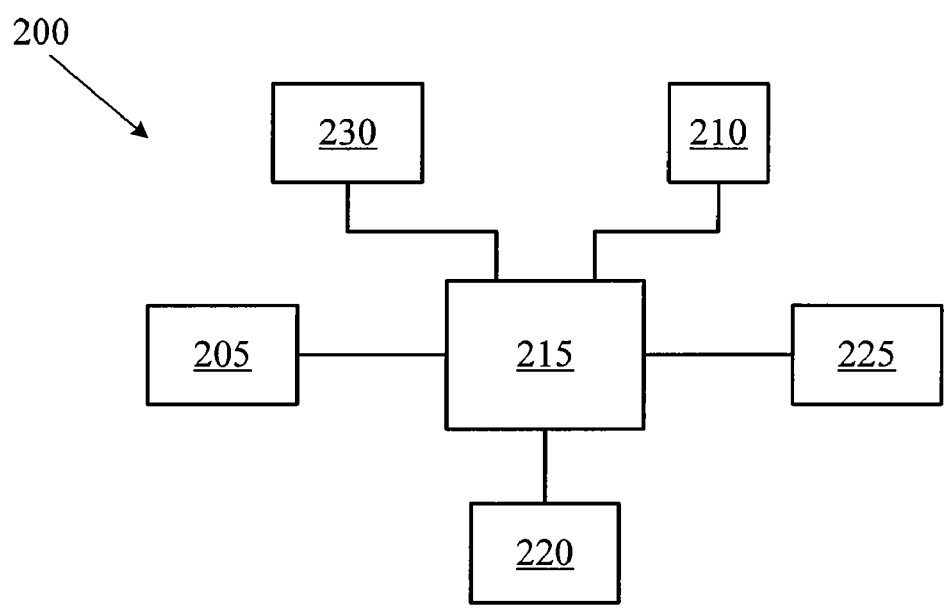
FIG. 2 is a block diagram of an IOP measuring system according to the principles of the present invention.

FIG. 2 is a block diagram of an IOP measuring system 200 according to the principles of the present invention. In FIG. 2, the IOP measuring system includes power source 205, IOP sensor 210, processor 215, memory 220, data transmission module 225, and optional speaker 230.

Power source 205 is typically a rechargeable battery, such as a lithium ion or lithium polymer battery, although other types of batteries may be employed. In addition, any other type of power cell is appropriate for power source 205. Power source 205 provides power to the system 200, and more particularly to processor 215. Power source can be recharged via an RFID link or other type of magnetic coupling.

Processor 215 is typically an integrated circuit with power, input, and output pins capable of performing logic functions. In various embodiments, processor 215 is a targeted device controller. In such a case, processor 215 performs specific control functions targeted to a specific device or component, such as a data transmission module 225, speaker 230, power source 205, or memory 220. In other embodiments, processor 215 is a microprocessor. In such a case, processor 215 is programmable so that it can function to control more than one component of the device. In other cases, processor 215 is not a programmable microprocessor, but instead is a special purpose controller configured to control different components that perform different functions.

Memory 220 is typically a semiconductor memory such as NAND flash memory. As the size of semiconductor memory is very small, and the memory needs of the system 200 are small, memory 220 occupies a very small footprint of system 200. Memory 220 interfaces with processor 215. As such, processor 215 can write to and read from memory 220. For example, processor 215 can be configured to read data from the IOP sensor 210 and write that data to memory 220. In this manner, a series of IOP readings can be stored in memory 220. Processor 215 is also capable of performing other basic memory functions, such as erasing or overwriting memory 220, detecting when memory 220 is full, and other common functions associated with managing semiconductor memory.

Data transmission module 225 may employ any of a number of different types of data transmission. For example, data transmission module 225 may be active device such as a radio. Data transmission module 225 may also be a passive device such as the antenna on an RFID tag. In this case, an RFID tag includes memory 220 and data transmission module 225 in the form of an antenna. An RFID reader can then be placed near the system 200 to write data to or read data from memory 220. Since the amount of data typically stored in memory 220 is likely to be small (consisting of IOP readings over a period of time), the speed with which data is transferred is not crucial. Other types of data that can be stored in memory 220 and transmitted by data transmission module 225 include, but are not limited to, power source data (e.g. low battery, battery defect), speaker data (warning tones, voices), IOP sensor data (IOP readings, problem conditions), and the like.

Optional speaker 230 provides a warning tone or voice to the patient when a dangerous condition exists. For example, if IOP is at a level that is likely to lead to damage or presents a risk to the patient, speaker 230 may sound a warning tone to alert the patient to seek medical attention or to administer eye drops. Processor 215 reads IOP measurements from IOP sensor 210. If processor 215 reads one or a series of IOP measurements that are above a threshold, then processor 215 can operate speaker 230 to sound a warning. The threshold can be set and stored in memory 220. In this manner, an IOP threshold can be set by a doctor, and when exceeded, a warning can be sounded.

Alternatively, data transmission module may be activated to communicate an elevated IOP condition to a secondary device such as a PDA, cell phone, computer, wrist watch, custom device exclusively for this purpose, remote accessible data storage site (e.g. an internet server, email server, text message server), or other electronic device. In one embodiment, a personal electronic device uploads the data to the remote accessible data storage site (e.g. an internet server, email server, text message server). Information may be uploaded to a remote accessible data storage site so that it can be viewed in real time, for example, by medical personnel. In this case, the secondary device may contain the speaker 230. For example, in a hospital setting, after a patient has undergone glaucoma surgery and had system 200 implanted, a secondary device may be located next to the patient's hospital bed. Since IOP fluctuations are common after glaucoma surgery (both on the high side and on the low side which is also a dangerous condition), processor 215 can read IOP measurements made by an implanted IOP sensor 210. If processor 215 reads an unsafe IOP condition, data transmission module 225 can alert the patient and medical staff via speaker 230 or by transmitting the unsafe readings to a secondary device.

Such a system is also suitable for use outside a hospital setting. For example, if an unsafe IOP condition exists, processor 215 can operate speaker 230 to sound an audible warning. The patient is then alerted and can seek medical attention. The warning can be turned off by a medical professional in a number of ways. For example, when data transmission module 225 is an RFID tag, an RFID link can be established between an external device and system 200. This external device can communicate with system 200 to turn off the speaker 230. Alternatively, an optical signal may be read by system 200. In this case, data transmission module 225 has an optical receptor that can receive a series of light pulses that represent a command—such as a command to turn off speaker 230.

System 200 is preferably in a small, implantable, integrated package. As such, all of the components of system 200 can be built on a substrate, such as a semiconductor wafer, by any of a number of different processes.

Figure 3:
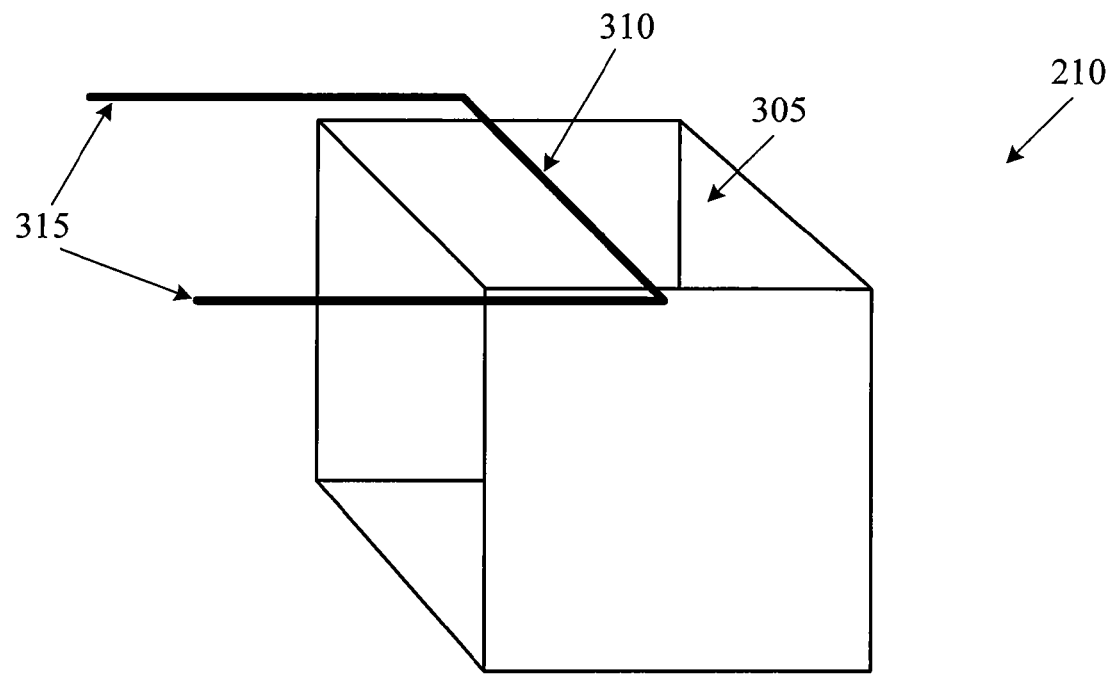
FIG. 3 is a perspective view of an IOP sensor according to the principles of the present invention.

FIG. 3 is a perspective view of an IOP sensor according to the principles of the present invention. In FIG. 3, IOP sensor 210 is a sealed cube with a strain gauge wire 310 embedded in top surface 305. Lead wires 315 allow a measurement to be taken that corresponds to IOP. The sealed cube has an internal pressure of about 0 psig or generally atmospheric pressure (although other pressures can be used as well, 0 psig is used as an example here). When IOP sensor 210 is exposed to the eye's aqueous humor, top surface 305 deflects inward because the eye's aqueous humor is at about ⅓ psig. In other words, when placed in the eye, there is a small pressure difference between the inside of the cube and the outside of the cube. Since the pressure inside the cube is lower than the pressure outside the cube, the top surface 305 deflects inward. Embedded strain gauge wire 310 is then stretched. As strain gauge wire 310 is stretched, its cross sectional area is reduced which causes a change in the measurable resistance of strain gauge wire 310. This change in resistance is measured via lead wires 315. In this manner, when a voltage is applied across lead wires 315, current can be measured to calculate the resistance of the strain gauge wire 310. Pressure can then be correlated to resistance so that a resistance measurement indicates a magnitude of IOP. While shown as a cube, IOP sensor may be other geometric shapes that allow for deflection of strain gauge wire 310.

The pressure inside the cube of IOP sensor 210 is determined during the manufacturing process and can be about 0 psig. The cube of IOP sensor 210 can be filled with any of a number of a variety of different gases, such as nitrogen, argon, sulfur hexafluoride, or the like.

For IOP measurements, calibrating the IOP sensor 210 is generally not critical. In most cases, it is the change in IOP that present problems for a glaucoma patient. Since a change in the resistance of strain gauge wire 310 can be correlated with a magnitude of IOP, a change in IOP can be easily detected. Generally, a series of resistance measurements taken over time corresponds to the relative magnitude of IOP over time. More precise calibration of IOP can be done in a doctor's office, for example, by measuring IOP in a traditional manner and correlating that measurement to a measured resistance of strain gauge wire 310.

IOP sensor 210 can be manufactured via any of a number of different methods. For example, in a MEMS-based method, IOP sensor 210 is built in layers. In this manner, layers of a biocompatible, flexible, electrically insulating material are deposited to build IOP sensor 210. When the top surface 305 is deposited, strain gauge wire 310 is embedded in the top surface 305. Other vapor deposition methods, such as those used in the semiconductor industry, may also be employed.

Figure 4:
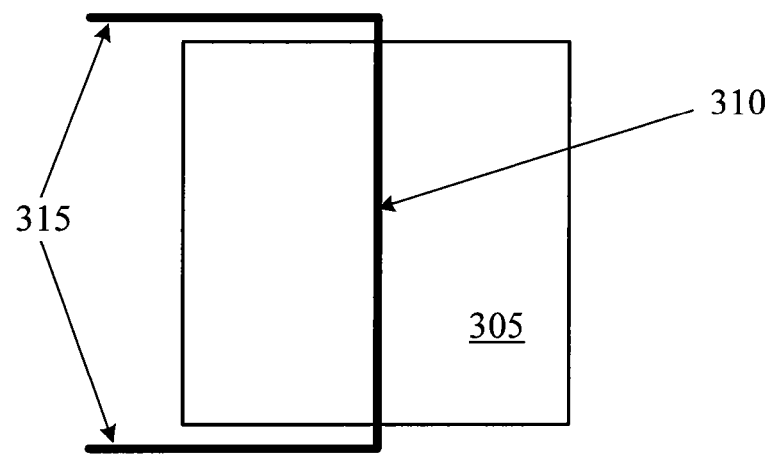
FIG. 4 is a top view of an IOP sensor according to the principles of the present invention.

FIG. 4 is a top view of an IOP sensor according to the principles of the present invention. In FIG. 4, strain gauge wire 310 is embedded in top surface 305 of the cube. Lead wires 315 are electrically coupled to strain gauge wire 310. While shown as a straight length of wire, strain gauge wire 310 may assume any configuration. For example, strain gauge wire 310 may be coiled, bent, looped, or assume a pattern on top surface 305. As top surface 305 is deflected inward, the length of strain gauge wire 310 changes resulting in a measurable change in resistance.

Figure 5:
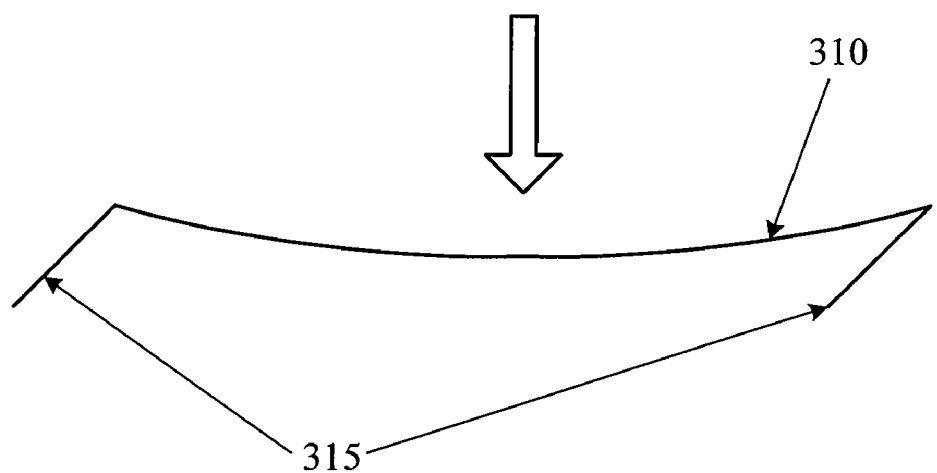
FIG. 5 is a representation of a strain gauge wire according to the principles of the present invention.

FIG. 5 is a representation of a strain gauge wire according to the principles of the present invention. In FIG. 5, strain gauge wire 310 is in a deflected position. The arrow represents the external pressure on IOP sensor 210. Since the external pressure is always greater than the internal pressure, strain gauge wire 310 will always be in some state of deflection.

Figure 6:
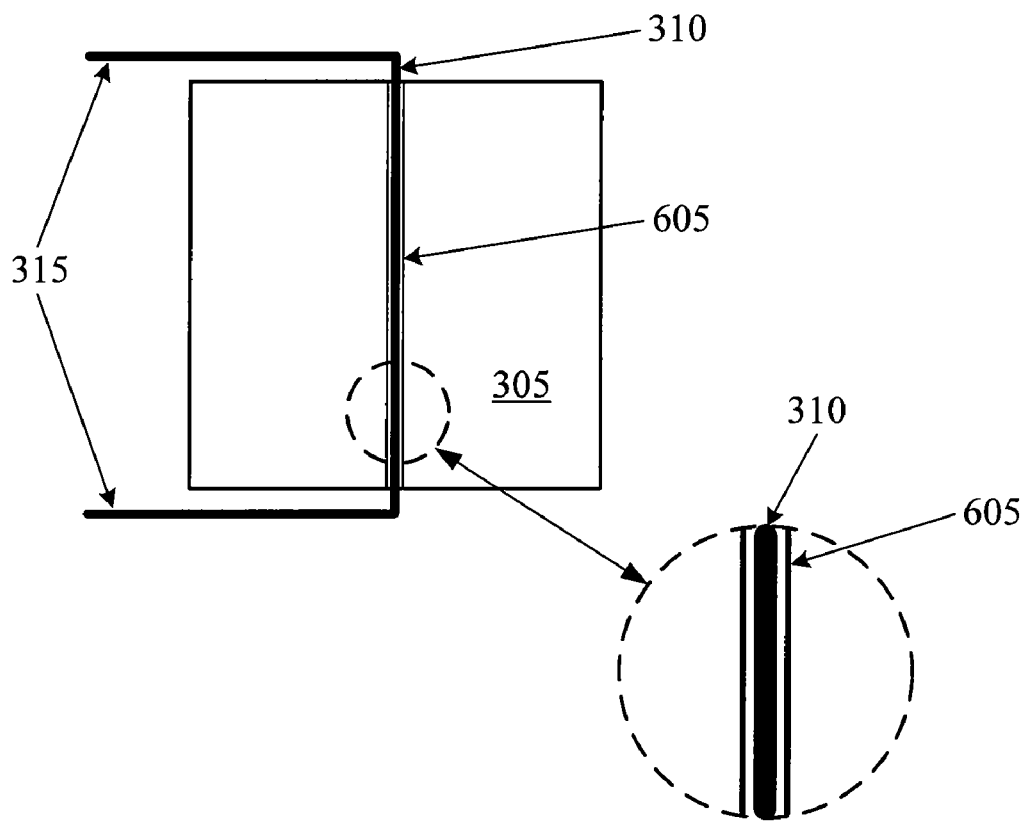
FIG. 6 is a top view of an IOP sensor according to the principles of the present invention.

FIG. 6 is a top view of an IOP sensor according to the principles of the present invention. In FIG. 6, strain gauge wire 310 is located in a track or groove 605 in top surface 305. This track or groove 605 assists in the manufacturability of IOP sensor 210. Since embedding strain gauge wire 310 in top surface 305 may be difficult depending on the type of manufacturing process used, a track or groove 605 may be manufactured in top surface 305 and a strain gauge wire 310 later placed in track or groove 605.

In another embodiment of the present invention, an array of IOP sensors 210 (shown in FIGS. 3 & 4) can be used together. In this configuration, more than one IOP sensor 210 is attached to a substrate and then implanted in the eye. Using more than one IOP sensor 210 allows for redundancy and more accurate measurement of IOP. As the number of IOP sensors 210 in array increases, the statistical variance of the resulting IOP measurement decreases (and thus accuracy increases).

From the above, it may be appreciated that the present invention provides a system measuring IOP. The present invention provides an IOP sensor and associated peripherals. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An implantable intraocular pressure sensor system comprising:
   a sealed geometric shape with an internal pressure at a first value, the sealed geometric shape having a surface;
   a strain gauge wire embedded in the surface;
   a processor electrically coupled to the strain gauge wire; and
   a speaker coupled to the processor;
   wherein when the surface is deflected a measured resistance of the strain gauge wire indicates an intraocular pressure, the processor is configured to read the measured resistance, the sealed geometric shape, the processor and the speaker are configured to be implanted into an anterior chamber of an eye, and the processor activates the speaker to sound a warning when the intraocular pressure is above a threshold pressure.

2. The pressure sensor system of claim 1 further comprising:
   a pair of lead wires, the pair of lead wires coupled to the strain gauge wire.

3. The pressure sensor system of claim 1 further comprising:
   a power source coupled to the processor; and
   a memory coupled to the processor.

4. The pressure sensor system of claim 3 wherein the processor writes values corresponding to intraocular pressure to the memory.

5. The pressure sensor system of claim 3 further comprising:
   a data transmission module coupled to the processor.

6. The pressure sensor system of claim 5 wherein the data transmission module further comprises a radio.

7. The pressure sensor system of claim 5 wherein the data transmission module further comprises an RFID tag.

8. The pressure sensor system of claim 5 wherein the data transmission module transfers data from the memory to an external device.

9. The pressure sensor system of claim 1 wherein the sealed geometric shape is generally cubic.

10. An implantable intraocular pressure sensor system comprising:
    an IOP sensor comprising:
       a sealed geometric shape with an internal pressure at a first value, the sealed geometric shape having a surface; and
       a strain gauge wire embedded in the surface;
       wherein when the surface is deflected by an intraocular pressure, a measured resistance of the strain gauge wire indicates the intraocular pressure;
    a processor electrically coupled to the strain gauge wire;
    a speaker coupled to the processor;
    a power source coupled to the processor; and
    a memory coupled to the processor;
       wherein the processor is configured to read the measured resistance and write values corresponding to intraocular pressure to the memory, the sealed geometric shape, the processor, the speaker, the power source, and the memory are configured to be implanted into an anterior chamber of any eye, and the processor activates the speaker to sound a warning when the intraocular pressure is above a threshold pressure.

11. The pressure sensor system of claim 10 further comprising:
    a data transmission module coupled to the processor.

12. The pressure sensor system of claim 11 wherein the data transmission module further comprises a radio.

13. The pressure sensor system of claim 11 wherein the data transmission module further comprises an RFID tag.

14. The pressure sensor system of claim 11 wherein the data transmission module transfers data from the memory to an external device.

15. The pressure sensor system of claim 10 wherein the sealed geometric shape is generally cubic.

16. The pressure sensor system of claim 1 wherein the warning is an indication to a patient to administer eye drops.

\* \* \* \* \*